United States Patent [19]
Nicholas

[11] Patent Number: 5,478,349
[45] Date of Patent: Dec. 26, 1995

[54] PLACEMENT OF ENDOPROSTHESES AND STENTS

[75] Inventor: Peter M. Nicholas, South Dartmouth, Mass.

[73] Assignee: Boston Scientific Corporation, Watertown, Mass.

[21] Appl. No.: 234,473

[22] Filed: Apr. 28, 1994

[51] Int. Cl.$^6$ .............................. A61M 29/00; A61F 2/04
[52] U.S. Cl. ................................. 606/198; 623/1; 623/12
[58] Field of Search ......................... 623/1, 12; 606/191, 606/192, 194, 195, 198, 200; 604/96; 128/899

[56] References Cited

U.S. PATENT DOCUMENTS

| | | |
|---|---|---|
| 3,657,744 | 4/1972 | Ersek . |
| 4,733,665 | 3/1988 | Palmaz . |
| 4,739,762 | 4/1988 | Palmaz . |
| 4,886,062 | 12/1989 | Wiktor . |
| 4,922,905 | 5/1990 | Strecker ................................ 623/12 |
| 5,019,090 | 5/1991 | Pinchuk . |
| 5,035,706 | 7/1991 | Giantureo et al. . |
| 5,102,417 | 4/1992 | Palmaz . |
| 5,122,154 | 6/1992 | Rhodes ................................ 606/198 |
| 5,133,732 | 7/1992 | Wiktor . |
| 5,192,297 | 3/1993 | Hull ........................................ 623/1 |

OTHER PUBLICATIONS

Strecker et al., "Expandable Tubular Stents for Treatment of Arterial Occlusive Diseases: Experimental and Clinical Results", Radiology, 175:97–102, (1990).

Barth et al., "Flexible Tantalum Stents Implanted in Aortas and Iliac Arteries: Effect in Normal Canines", Radiology, 175:91–96, (1990).

Primary Examiner—Tamara L. Graysay
Assistant Examiner—William Lewis
Attorney, Agent, or Firm—Fish & Richardson

[57] ABSTRACT

A method and device for implanting an endoprosthesis within the lumen of a body passageway. A tubular, elongated endoprosthesis having a small outer diameter for intraluminal delivery of the selected body passageway, is capable of being progressively permanently deformed to an expanded diameter by application of outwardly acting force. The endoprosthesis is provided on a catheter having an inflatable, radially expandable balloon, the axial dimension of which is shorter than the axial dimension of the endoprosthesis. The elongated prothesis is inserted in unexpanded state into a desired location within the body passageway and with the catheter positioned so that its expandable portion registers inside a first portion of the endoprosthesis, the inflatable portion of the catheter is inflated to cause deformation of the first portion of the endoprosthesis to an expanded diameter. The inflatable portion of the catheter is then deflated and shifted axially until it registers with an unexpanded portion of the endoprosthesis and the inflation of the inflatable portion of the catheter is repeated until the elongated endoprosthesis is expanded the desired length, and the endoprosthesis is permanently placed within the lumen. With the endoprosthesis comprised at least partically of knitted wire, the long endoprosthesis is especially capable of conforming to tortuosities of the body passage.

14 Claims, 5 Drawing Sheets

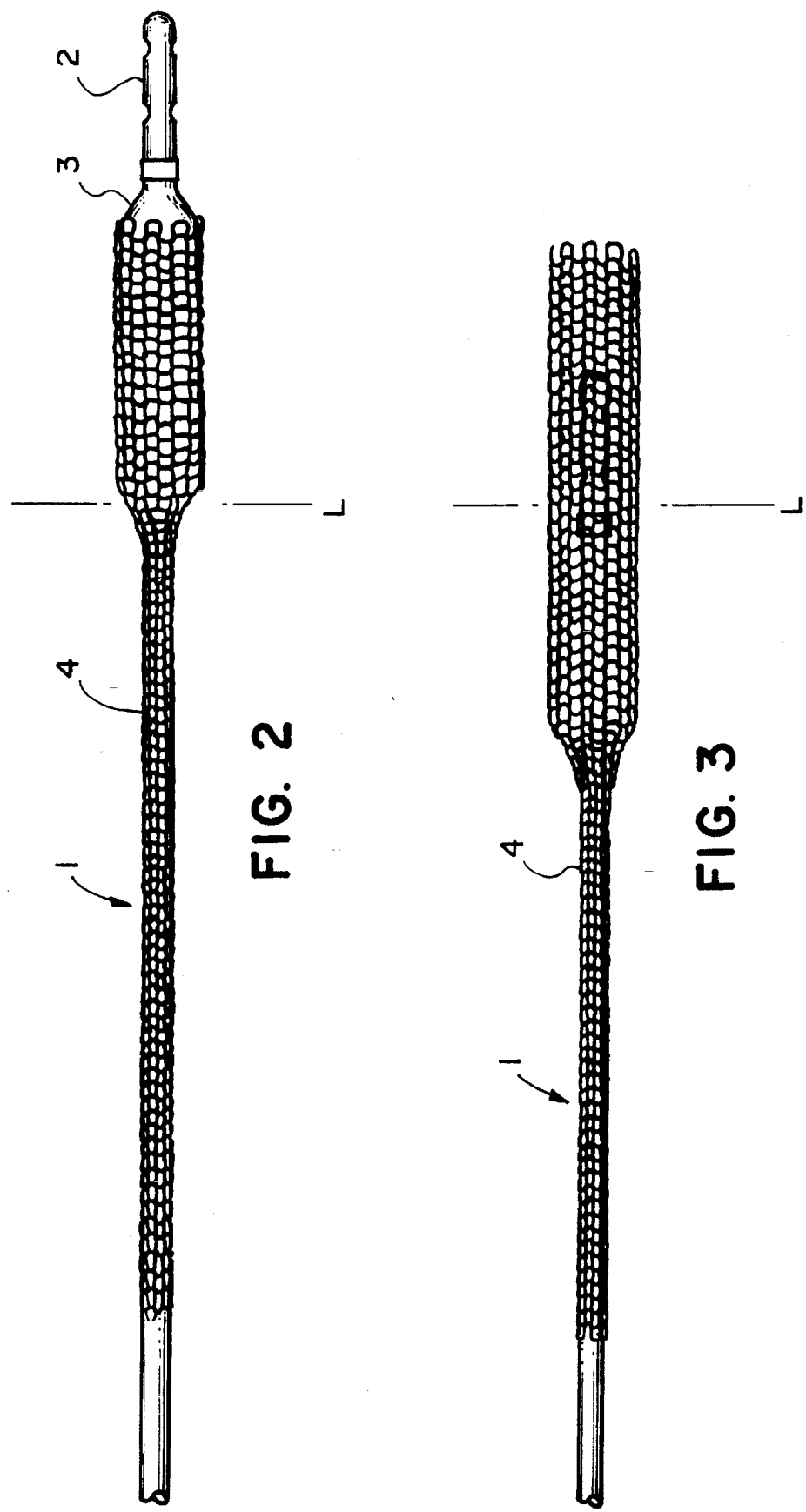

PLACEMENT OF ENDOPROSTHESES AND STENTS

BACKGROUND OF THE INVENTION

The invention relates to placement of tubular endoprostheses or stents for body passages, particularly for opening, dilating and maintaining blood vessels and other biological ducts which are at risk of closure due to flaps, dissections, loose vessel debris, etc.

The general use of endoprostheses for such purposes is well known. In one technique a tubular endoprosthesis is mounted over an inflatable balloon of corresponding length, which is part of a disposable balloon catheter. The catheter is inserted into a vessel or duct and guided to the desired site. The balloon is then expanded to expand and permanently secure the endoprosthesis at the site. After this the balloon is deflated and the catheter is withdrawn to complete the placement sequence, and the balloon catheter is discarded. When the region of the blood vessel or duct requires placement over a length greater than the length of a standard prosthesis, often two of the prostheses are placed by their respective balloon catheters in end-to-end relationship with some overlap. This requires two separate placement sequences, requires the use of two disposable balloon catheters, and creates a number of problems both in placement and in use. Other techniques seeking to use long endoprostheses and stents have had drawbacks related to placement or use.

SUMMARY OF THE INVENTION

I have provided a long tubular endoprosthesis which is longer than its expansion balloon, and have provided for selective inflation, deflation, axial shifting of position and reinflation of the inflation balloon to progressively expand the endoprosthesis to place it in a duct or vessel section. In particularly preferred embodiments the endoprosthesis is a stent of knitted construction.

More particularly, according to one aspect of the invention, I provide a method and device for implanting an endoprosthesis within the lumen of a body passageway comprising providing a tubular shaped, elongated endoprosthesis having a small first diameter which permits intraluminal delivery of the endoprosthesis into a selected body passageway, the endoprosthesis being capable of being progressively permanently deformed to an expanded diameter upon application of radial, outwardly acting force applied to the interior wall of the endoprosthesis; providing a catheter having an inflatable, radially expandable portion, the axial dimension of which is shorter than the axial dimension of the endoprosthesis; inserting the elongated prothesis in unexpanded state into a desired location within the body passageway; with the catheter positioned within the endoprosthesis so that its expandable portion registers with a first portion of the endoprosthesis, inflating the inflatable portion of the catheter to cause the deformation of the first portion of the endoprosthesis to a second, expanded diameter; causing the deflation of the inflatable portion of the catheter; axially shifting the inflatable portion of the catheter within the endoprosthesis while the inflatable portion is in deflated state until the inflatable portion registers with an unexpanded portion of the endoprosthesis; and repeating the inflation of the inflatable portion of the catheter at least one additional time until the elongated endoprosthesis is expanded throughout the desired length, and the endoprosthesis is permanently placed in supporting relationship within the lumen of the body passageway; and thereafter withdrawing the catheter.

Preferred embodiments of this aspect of the invention have one or more of the following features.

Prior to insertion of the endoprosthesis into the body, the elongated endoprosthesis is mounted in unexpanded state over the inflatable portion of the catheter, the inflatable portion of the catheter being in deflated state. The catheter is then inserted into the body to place the endoprosthesis in the desired location.

The first portion of the endoprosthesis has an initial unexpanded diameter smaller than the unexpanded diameter of remaining portions of the endoprosthesis such that the initial diameter of the first portion secures the endoprosthesis upon the expandable portion of the catheter for insertion, and the diameter of the remaining portions of the endoprosthesis enables the catheter, after expansion of the first portion of the endoprosthesis, to be moved axially within the endoprosthesis when the inflatable portion is in at least a partially deflated state.

Alternatively, the endoprosthesis in unexpanded state is of uniform size and is detachably secured over the inflatable portion prior to insertion into the body.

In one preferred embodiment, the endoprosthesis is secured by partially inflating the inflatable portion sufficiently to secure the endoprosthesis to the catheter prior to insertion into the body.

The long endoprosthesis is preferably of knitted construction enabling it to conform to tortuosities of the duct.

According to another aspect of the invention, a medical device is provided comprising a tubular shaped, elongated knitted stent having a small first diameter which permits intraluminal delivery of the stent into a selected body passageway, the stent being capable of progressive permanent deformation to an expanded diameter upon application of radial, outwardly acting force applied to the interior wall surface of the stent; a catheter having an inflatable, radially expandable portion associated therewith, the axial dimension of which being shorter than the axial dimension of the stent; the elongated stent being detachably mounted in unexpanded state on the catheter with the inflatable portion of the catheter disposed within a first portion of the stent which is to be first expanded.

Furthermore, according to the present invention, I have realized that disadvantages of prior techniques can be overcome by employing a longer than usual endoprosthesis and an axially movable balloon intentionally substantially shorter than the endoprosthesis. The same balloon is then employed to inflate different sections of the endoprosthesis, by axially shifting the balloon within the endoprosthesis between inflations.

Prior art expandable tubular endoprostheses, and in particular vascular stents, have often ranged from 2–14 mm diameter and generally have been limited to about 8 cm in length because of limits on practical balloon length. As the length of the balloon increases, uniform balloon expansion is difficult to achieve, and if the balloon is too long it will cause the endoprosthesis to be expanded in a non-uniform, undesirable way.

One of the advantages of the technique I have provided is that it can ensure uniform expansion throughout the length of a long endoprosthesis. Another advantage is avoiding the time-consuming step of overlapping one endoprosthesis over the next. Avoidance of overlap furthermore avoids rigidity and reduced flexibility of the endoprosthesis at the region of the overlap, and therefore avoids differences in compliance created along the length of the vessel. Differences in compliance have been shown by vascular surgeons to create areas where stenosis becomes more aggressive. The invention can also avoid a decrease in the diameter of the lumen at the overlap which may present blood flow abnormalities and lead to increased likelihood of thrombosis. The invention also eliminates the need, after each section of endoprosthesis is positioned, to remove the catheter from the patient's body and insert a new catheter and endoprosthesis and thus can reduce the duration of the procedure and the patient's risk of infection.

According to the invention, a balloon of standard length may be employed to place any length endoprosthesis. The surgeon simply inflates the balloon to dilate one section of the endoprosthesis, deflates the balloon, moves the balloon distally a distance slightly short of one balloon length, then reinflates the balloon, and repeats this procedure until the entire length of the endoprosthesis is expanded. Such a standard length balloon can be selected to be relatively short, which can facilitate placement of long endoprostheses to severely tortuous pathways. Placement in such tortuous pathways is particularly effective when the stent is of knitted construction.

BRIEF DESCRIPTION OF THE DRAWING

FIG. 2 shows the endoprosthesis of FIG. 1 with the dilation balloon expanded at the distal end as a result of the first expansion stage during the insertion procedure.

FIG. 3 shows the endoprosthesis of FIG. 1 expanded for a distance of about two balloon lengths as a result of the second stage of expansion.

DESCRIPTION OF THE PREFERRED EMBODIMENT(S)

Figure 1:
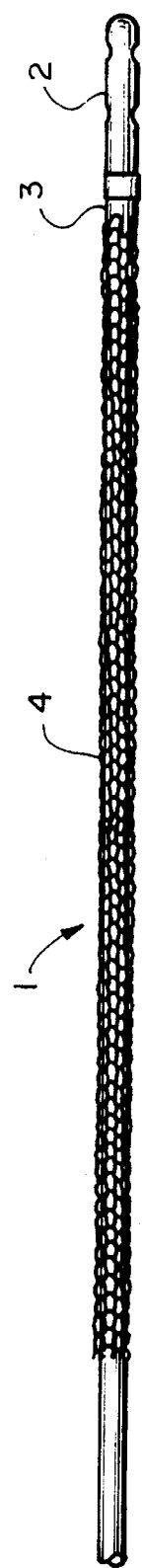
FIG. 1 shows an unexpanded endoprosthesis mounted on the distal end of a dilation balloon.
Figure 1A:
FIG. 1a shows the long unexpanded endoprosthesis component of the device of FIG. 1 of length $L_E$.
Figure 1B:
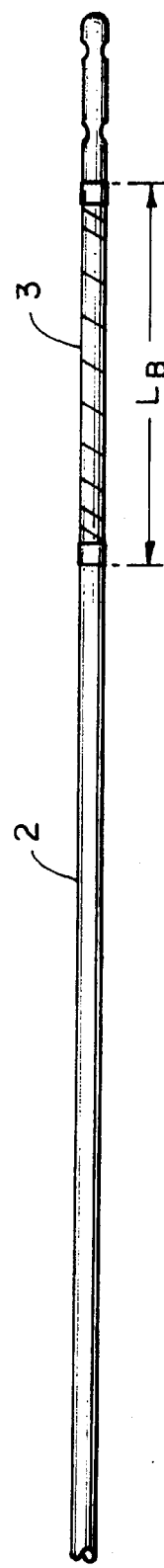
FIG. 1b shows the balloon catheter component of the device of FIG. 1 with a relatively short deflated dilation balloon of length $L_B$.
Figure 1C:
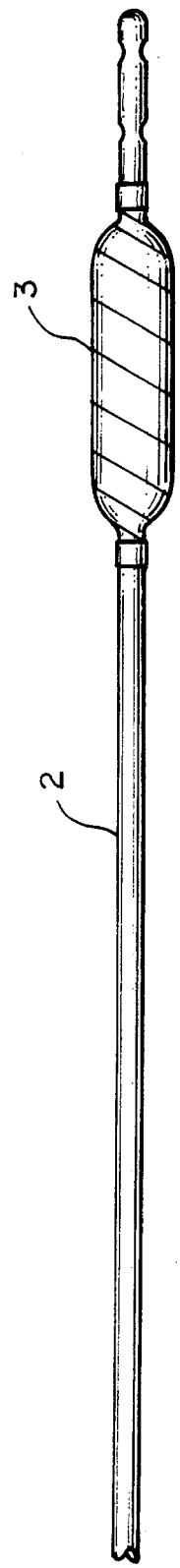
FIG. 1c shows the balloon catheter of FIG. 1b with the dilation balloon inflated.

Referring to FIGS. 1–3, in the preferred embodiment, the device 1 comprises catheter body 2 upon which a standard 4 cm length dilation balloon 3 is mounted, as shown in FIG. 1b. A 17 cm length, 14 mm diameter endoprosthesis 4 is disposed over the catheter with the endoprosthesis 4 registering with the distal end of the balloon. The length $L_E$ of endoprosthesis 4 is substantially longer than the length $L_B$ of dilation balloon 3, as shown in FIGS. 1a and 1b. The endoprosthesis 4 is knitted from a biocompatible, corrosion resistant, negatively charged, highly radiopaque material (e.g., tantalum). The dilation balloon 3 is of a set inflated dimension and is formed of a non-compliant or inelastic material (e.g., polyethylene or polyethylene teraphalatate) which is folded into a small dimension, and inserted into the distal end of the stent where it is secured, as shown in FIG. 1. After placement, upon inflation, the dilation balloon 3 unfolds until it reaches a maximum dimension as shown by itself in FIG. 1c. During the first stage of inflation, the condition of FIG. 2 is achieved. After deflation and proximal axial shifting of the catheter one balloon length to the left to position L, the stent is expanded again to achieve the condition of FIG. 3. Thereafter successive deflating, axially shifting and reinflating after each inflation stage enables complete expansion of the stent.

Figure 4:
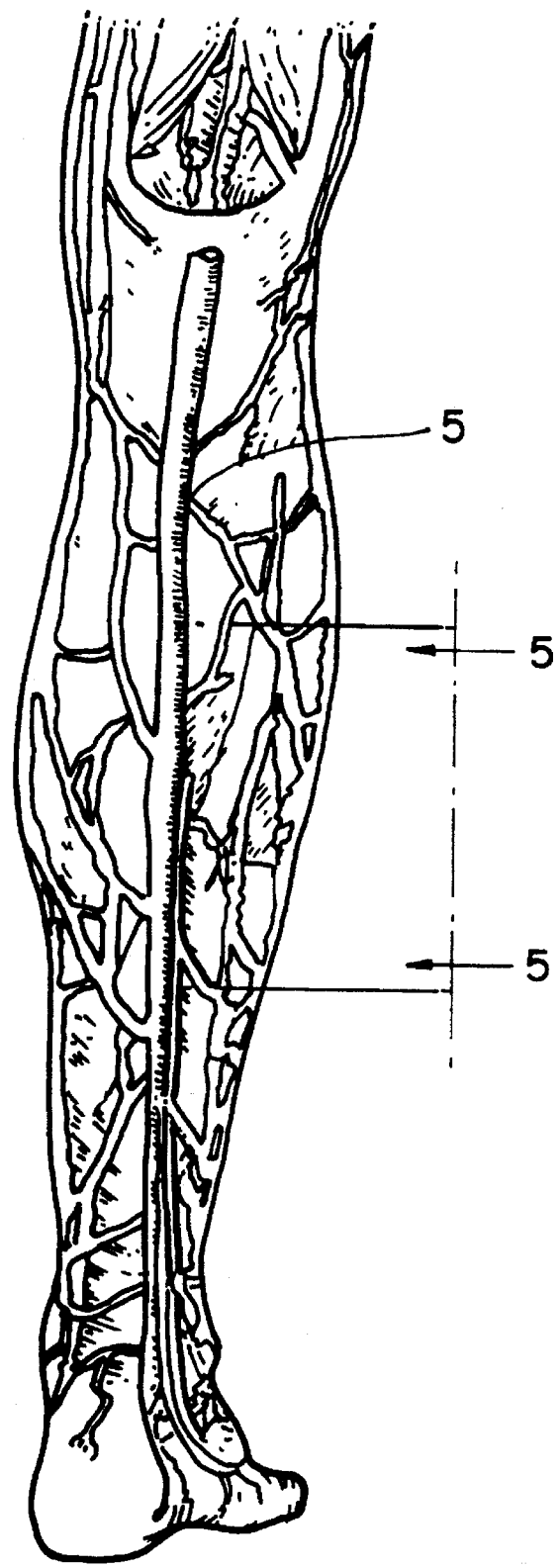
FIG. 4 is a rear view of a partially occluded small saphenous vein.

Referring now to FIG. 4, the endoprosthesis 4 may be used in the longer veins and arteries of the body (e.g., the small saphenous vein 5 of the leg) to reestablish or improve patency of an occluded lumen. The endoprosthesis 4 may be secured by the physician to the dilation balloon 3 and catheter body 2. Preferably the manufacturer provides a preassembled unit with the distal end of the endoprosthesis prepositioned over the balloon at the distal end of the catheter. The device 1 is inserted into the femoral vein in the groin area and under fluoroscopic observation guided into the small saphenous vein 5 in the lower leg calf region.

Figure 5:
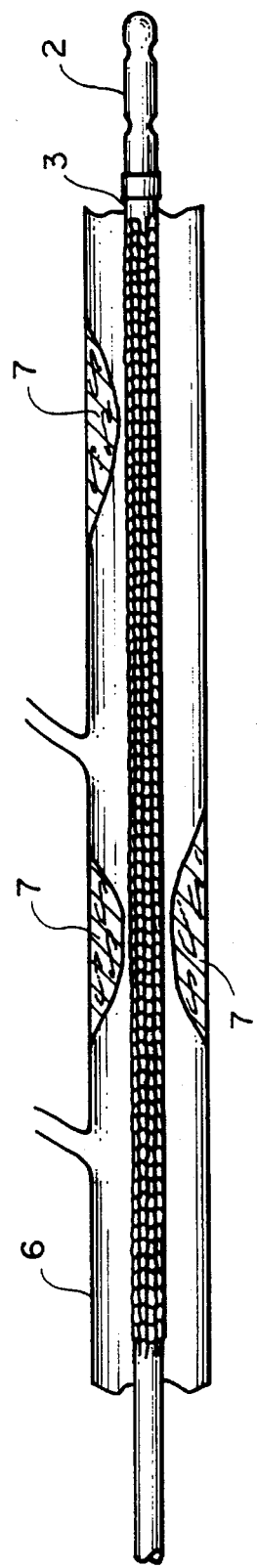
FIG. 5 is longitudinal diagrammatic cross sectional view of enlarged scale of the vein of FIG. 4 taken along line 5—5 with the unexpanded endoprosthesis in place, with the dilation balloon at the distal end of the treatment site.
Figure 6:
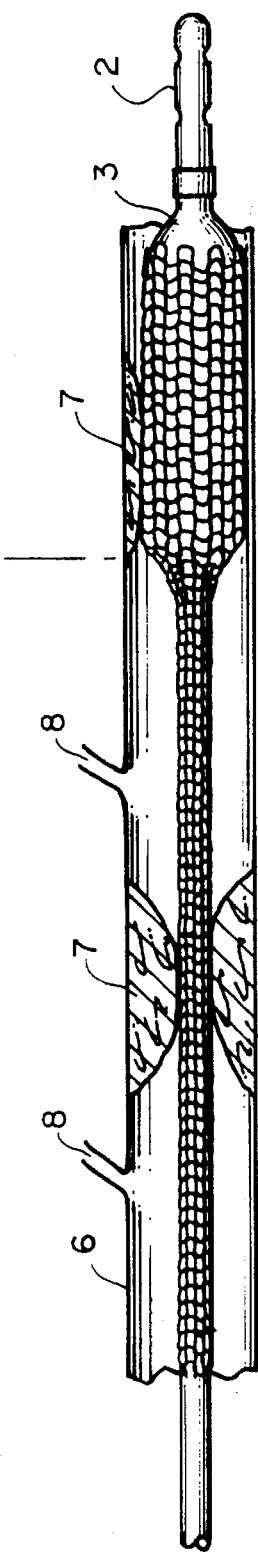
FIG. 6 is a view similar to FIG. 5 with the dilation balloon expanded in the first stage of expansion.
Figure 7:
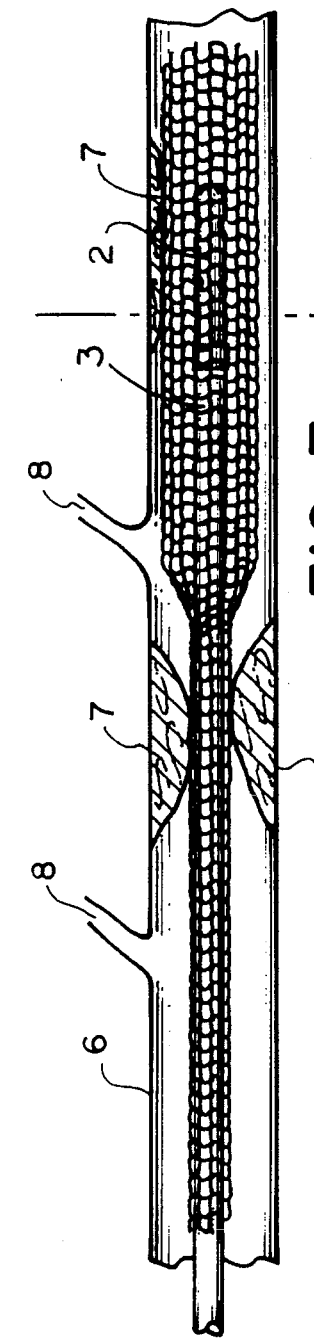
FIG. 7 is a view similar to FIG. 5 with the endoprosthesis expanded about two balloon lengths as a result of the second stage expansion.
Figure 8:
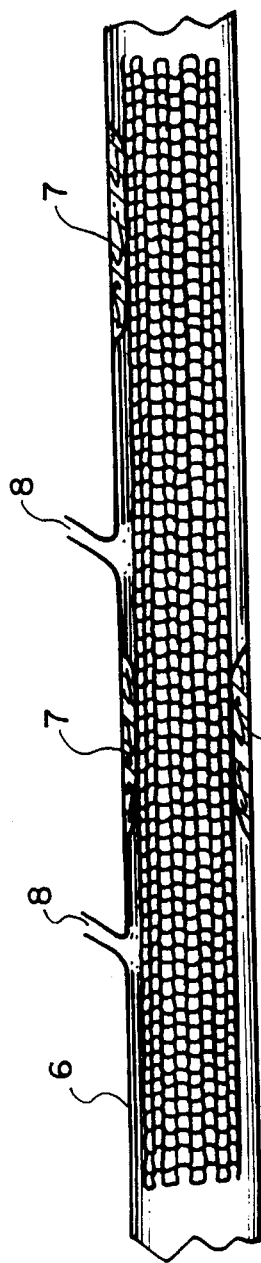
FIG. 8 shows the endoprosthesis fully expanded and the catheter withdrawn.

Referring now to FIGS. 5–8, small saphenous vein 5 is occluded with plaque deposits 7 on vein wall 6. The device 1 is maneuvered along small saphenous vein 5 to position the distal end of endoprosthesis 4 at the distal end of the treatment site, as shown in FIG. 5. The dilation balloon 3 is then inflated to radially expand, permanently deform, and position the distal end of endoprosthesis 4, thereby outwardly, radially compressing plaque deposits 7, as shown in FIG. 6. The dilation balloon 3 is then deflated by the physician and dilation balloon 3 and catheter 2 are then moved proximally within endoprosthesis 4 slightly less than one balloon length to position L and inflated again, as shown in FIG. 7. This procedure is repeated until endoprosthesis 4 is radially expanded throughout its length and securely positioned, as shown in FIG. 8. After the entire length of endoprosthesis 4 is positioned, the dilation balloon 3 is deflated its final time and the catheter body 2 and dilation balloon 3 are removed from the patient. This preferred embodiment is particularly advantageous in that the open-knit design of the endoprosthesis 4 conforms to tortuous and contoured lumen walls without blocking side branches 8 and provides cross-sectional elasticity and high resistance to deformation. For further information concerning knitted stents in general see Strecker U.S. Pat. No. 4,922,905, which is hereby incorporated by reference.

Figure 9:
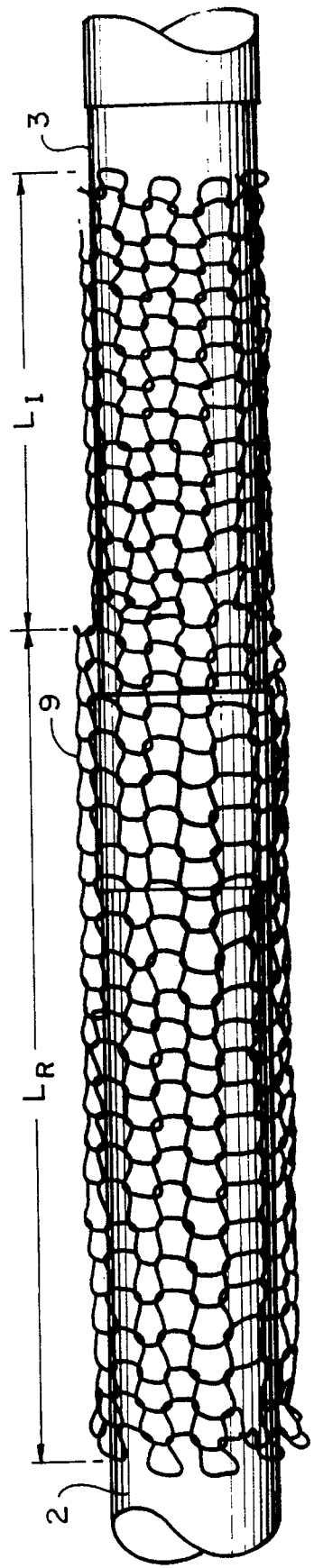
FIG. 9 shows an endoprosthesis with an initial unexpanded length $L_I$ of smaller diameter than the unexpanded remaining length $L_R$.

Referring now to FIG. 9, endoprosthesis 9 has an initial unexpanded length $L_I$ of slightly smaller diameter than the diameter of the unexpanded remaining length $L_R$ to secure endoprosthesis 9 on catheter body 2 over the standard length dilation balloon 3.

ALTERNATIVE EMBODIMENTS

In another embodiment the balloon is fully deflated during placement and the stent in unexpanded form is secured to the catheter by overlapping resilient tubular members at the ends of the stent, constructed to release the distal end of the stent upon the first stage of inflation of the balloon, at the distal end, upon the first expansion of the stent, and to release the proximal end by the first step of axial movement of the catheter relative to the stent. Similar overlapping members are described in U.S. Pat. No. 4,950,227 assigned to Boston Scientific Corporation.

In another embodiment, endoprosthesis 4 may be of a partially or totally self-expanding type. The dilation balloon 3 is then used to supplement the self-expansive forces of the endoprosthesis to assure full permanent expansion and secure positioning, rather than to provide the sole expansive force to position the endoprosthesis, as in the first preferred embodiment.

The knitted structure of the preferred embodiments mentioned above has attributes important to the realization of the full benefits of the invention, some of which have been mentioned above, especially the adaptability to long tortuous vessels, the ability to secure definite placement without change in length of the endoprosthesis or stent during placement, and the compliance with movement of the body, without dislodgement.

Nevertheless, in addition to the preferred tube-like knitted structure, the endoprosthesis 4 may also be made by crocheting, weaving, knotting, or forming by other means, and by other filament material. The endoprosthesis 4 adapted for vascular use may range for instance from 2–15 mm in diameter and 10–30 cm in length.

What is claimed is:

1. A medical device comprising a continuous, tubular shaped stent of extended length comprised of filament material extending throughout said length, said filaments being interconnected at a multiplicity of points along said length, said stent having a small first diameter which permits intraluminal delivery of the stent into a selected body passageway, the stent being capable of progressive permanent deformation to an expanded diameter upon application of radial, outwardly acting force applied to the interior wall surface of the stent;

a stent-expanding catheter having an inflatable, radially expandable portion associated therewith, the axial dimension of which being shorter than the length of the stent, the stent being detachably mounted in unexpanded state on the catheter with the inflatable portion of the catheter disposed within a first portion of the stent which is to be first expanded.

2. The medical device of claim 1 wherein the first portion of the endoprosthesis has an initial unexpanded diameter smaller than the unexpanded diameter of remaining portions of the endoprosthesis such that the initial diameter of the first portion secures the endoprosthesis upon the expandable portion for insertion and the diameter of the remaining portions of the endoprosthesis enables the catheter to move axially within the endoprosthesis after the first portion of the endoprosthesis is expanded.

3. A medical device comprising a tubular shaped, elongated endoprosthesis having a small first diameter which permits intraluminal delivery of the endoprosthesis into a selected body passageway, the endoprosthesis being capable of progressive permanent deformation to an expanded diameter upon application of radial, outwardly acting force applied to the interior wall surface of the endoprosthesis;

a catheter having an inflatable, radially expandable portion associated therewith, the axial dimension of which being shorter than the axial dimension of the endoprosthesis, the elongated endoprosthesis being detachably mounted in unexpanded state on the catheter with the inflatable portion of the catheter disposed within a first portion of the endoprosthesis which is to be first expanded, wherein the first portion of the endoprosthesis has an initial unexpanded diameter smaller than the unexpanded diameter of remaining portions of the endoprosthesis such that the initial diameter of the first portion secures the endoprosthesis upon the expandable portion for insertion and the diameter of the remaining portions of the endoprosthesis enables the catheter to move axially within the endoprosthesis after the first portion of the endoprosthesis is expanded.

4. The device of claims 1 or 3 wherein the endoprosthesis comprises a vascular stent.

5. A method for implanting a stent within the lumen of a body passageway, comprising:

providing a continuous, tubular shaped stent of extended length comprised of filament material extending throughout said length, said filament material being interconnected at a multiplicity of points along said length, said stent having a small first diameter which permits intraluminal delivery of the stent into a selected body passageway, the stent being capable of being progressively permanently deformed to a second, expanded diameter upon application of radial, outwardly acting force applied to the interior wall of the stent;

providing a catheter having at least one inflatable, radially expandable portion;

inserting the stent in unexpanded state into a desired location within the body passageway;

with the catheter positioned within the stent so that said inflatable portion of said catheter registers with only a first portion of the stent shorter than the overall length of the stent, inflating said inflatable portion of the catheter to cause the deformation of said filaments of said first portion of the stent to cause said first portion of said stent to reach said second, expanded diameter, the remainder of said stent continuing to have said first diameter with the filaments thereof remaining integrally joined to the filaments of said first portion;

causing the deflation of said inflatable portion of the catheter;

shifting the catheter axially within the stent until said inflatable portion of the catheter registers with a second, unexpanded portion of the stent; and inflating said inflatable portion of the catheter to expand said second, unexpanded portion, whereby said first portion and said second portion of said stent are inflated to said second, expanded diameter.

6. The method of claim 5 in which said steps are repeated until the elongated endoprosthesis is expanded throughout the desired length, and the endoprosthesis is permanently placed in supporting relationship within the lumen of the body passageway;

and thereafter withdrawing the catheter.

7. The method of claim 5 wherein prior to insertion of the endoprosthesis into the body, the elongated endoprosthesis is mounted in unexpanded state over the inflatable portion of the catheter, the inflatable portion of the catheter being in deflated state;

and inserting the catheter into the body to place the endoprosthesis in the desired location.

8. The method of claim 7 wherein the first portion of the endoprosthesis has an initial unexpanded diameter smaller than the unexpanded diameter of remaining portions of the endoprosthesis such that the initial diameter of the first portion secures the endoprosthesis upon the expandable portion of the catheter for insertion, and the diameter of the remaining portions of the endoprosthesis enables the catheter, after expansion of the first portion of the endoprosthesis, to be moved axially within the endoprosthesis when the inflatable portion is in at least a partially deflated state.

9. The method of claim 7 wherein the endoprosthesis in unexpanded state is of uniform size and the endoprosthesis is detachably secured over the inflatable portion prior to insertion into the body.

10. The method of claim 9 wherein the endoprosthesis is secured by partially inflating the inflatable portion sufficiently to secure the endoprosthesis to the catheter prior to insertion into the body.

11. The method of claim 5 wherein said first portion and said second portion of said stent are adjoining portions of said stent.

12. A method for implanting an endoprosthesis within the lumen of a body passageway, comprising:

providing a tubular shaped, elongated endoprosthesis having a small first diameter which permits intraluminal delivery of the endoprosthesis into a selected body passageway, the endoprosthesis being capable of being progressively permanently deformed to an expanded diameter upon application of radial, outwardly acting force applied to the interior wall of the endoprosthesis;

providing a catheter having at least one inflatable, radially expandable portion;

mounting the elongated endoprosthesis in unexpanded state over the inflatable portion of the catheter, the inflatable portion of the catheter being in deflated state;

and inserting the catheter into the body to place the endoprosthesis in the desired location;

with the catheter positioned within the endoprosthesis so that said inflatable portion of said catheter registers with a first portion of the endoprosthesis shorter than the overall length of the endoprosthesis, inflating said inflatable portion of the catheter to cause the deformation of said first portion of the endoprosthesis to a second, expanded diameter;

causing the deflation of said inflatable portion of the catheter;

shifting the catheter axially within the endoprosthesis until said inflatable portion of said catheter registers with a further, unexpanded portion of the endoprosthesis; and inflating said inflatable portion of said catheter to expand said further, unexpanded portion;

wherein the first portion of the endoprosthesis has an initial unexpanded diameter smaller than the unexpanded diameter of remaining portions of the endoprosthesis such that the initial diameter of the first portion secures the endoprosthesis upon the inflatable portion of the catheter for insertion, and the diameter of the remaining portions of the endoprosthesis enables the catheter, after expansion of the first portion of the endoprosthesis, to be moved axially within the endoprosthesis when the inflatable portion is in at least a partially deflated state.

13. A method for implanting an endoprosthesis within the lumen of a body passageway, comprising:

providing a tubular shaped, elongated endoprosthesis having a small first diameter which permits intraluminal delivery of the endoprosthesis into a selected body passageway, the endoprosthesis being capable of being progressively permanently deformed to an expanded diameter upon application of radial, outwardly acting force applied to the interior wall of the endoprosthesis, the endoprosthesis in unexpanded state being of uniform size;

providing a catheter having at least one inflatable, radially expandable portion;

detachably securing the elongated endoprosthesis in unexpanded state over the inflatable portion of the catheter, the inflatable portion of the catheter being in deflated state, securing the endoprosthesis by partially inflating the inflatable portion sufficiently to secure the endoprosthesis to the catheter;

and inserting the catheter into the body to place the endoprosthesis in the desired location;

with the catheter positioned within the endoprosthesis so that said expandable portion of said catheter registers with a first portion of the endoprosthesis shorter than the overall length of the endoprosthesis, inflating said inflatable portion of said catheter to cause the deformation of said first portion of the endoprosthesis to a second, expanded diameter;

causing the deflation of said inflatable portion of the catheter;

shifting the catheter axially within the endoprosthesis until said inflatable portion of said catheter registers with a further, unexpanded portion of the endoprosthesis; and inflating said inflatable portion of said catheter to expand said further unexpanded portion.

14. The method of claims 5, 12 or 13 wherein the endoprosthesis is for use in a blood vessel.

* * * * *